(12) United States Patent  (10) Patent No.: US 8,535,292 B2
Tollner et al.  (45) Date of Patent: Sep. 17, 2013

(54) RETRACTABLE CATHETER

(75) Inventors: Thomas Tollner, Karlsruhe (DE); Martin Wubbeling, Mannheim (DE)

(73) Assignee: C. R. Bard, Inc., Murray Hill, NJ (US)

( * ) Notice: Subject to any disclaimer, the term of this patent is extended or adjusted under 35 U.S.C. 154(b) by 312 days.

(21) Appl. No.: 12/630,156

(22) Filed: Dec. 3, 2009

(65) Prior Publication Data

US 2010/0145309 A1 Jun. 10, 2010

Related U.S. Application Data

(60) Provisional application No. 61/119,668, filed on Dec. 3, 2008.

(30) Foreign Application Priority Data

Dec. 3, 2008 (GB) .................................. 0822106.1

(51) Int. Cl.
*A61M 25/00* (2006.01)
*B23P 17/04* (2006.01)

(52) U.S. Cl.
USPC ............................................. 604/524; 29/428

(58) Field of Classification Search
USPC ............ 604/524, 525, 526, 527, 523; 29/428
See application file for complete search history.

(56) References Cited

U.S. PATENT DOCUMENTS

| 5,534,007 | A | 7/1996 | St. Germain et al. |
| 5,545,132 | A | 8/1996 | Fagan et al. |
| 5,649,908 | A | 7/1997 | Itoh |
| 5,741,429 | A | 4/1998 | Donadio, III et al. |
| 5,797,889 | A * | 8/1998 | Steinman ...................... 604/533 |
| 5,797,952 | A | 8/1998 | Klein |
| 5,833,694 | A | 11/1998 | Poncet |
| 6,285,903 | B1 | 9/2001 | Rosenthal et al. |
| 7,029,468 | B2 * | 4/2006 | Honebrink ..................... 604/528 |
| 7,232,452 | B2 * | 6/2007 | Adams et al. ................. 606/200 |
| 2001/0027323 | A1 | 10/2001 | Sullivan et al. |
| 2004/0064179 | A1 | 4/2004 | Linder et al. |
| 2004/0193141 | A1 | 9/2004 | Leopold et al. |
| 2004/0193243 | A1 | 9/2004 | Mangiardi et al. |
| 2004/0220653 | A1 | 11/2004 | Borg et al. |
| 2005/0004553 | A1 | 1/2005 | Douk |

(Continued)

FOREIGN PATENT DOCUMENTS

| EP | 0165963 A1 | 1/1986 |
| EP | 0611556 A1 | 8/1994 |

(Continued)

OTHER PUBLICATIONS

EP 06754410.6 filed Jun. 16, 2006 Office Action dated Aug. 18, 2010.

(Continued)

*Primary Examiner* — Kevin C Sirmons
*Assistant Examiner* — Michael J Anderson
(74) *Attorney, Agent, or Firm* — Rutan & Tucker, LLP

(57) ABSTRACT

A retractable catheter for use in an implant delivery system, the catheter including an elongate tubular sheath made of a relatively flexible material, and a pull element for transmitting a pull force to the sheath to retract it longitudinally. The pull element includes an end portion disposed in the relatively flexible material, at least the thickness of the end portion being substantially less than its length.

21 Claims, 2 Drawing Sheets

(56) References Cited

U.S. PATENT DOCUMENTS

| | | |
|---|---|---|
| 2005/0049682 A1 | 3/2005 | Leanna et al. |
| 2005/0059957 A1* | 3/2005 | Campbell et al. ............. 604/524 |
| 2005/0124917 A1* | 6/2005 | Skujins et al. ................ 600/585 |
| 2006/0184107 A1* | 8/2006 | Bencini et al. ............ 604/95.04 |
| 2006/0216431 A1 | 9/2006 | Kerrigan |
| 2006/0247661 A1 | 11/2006 | Richards et al. |
| 2006/0263145 A1* | 11/2006 | Pal ................................... 403/1 |
| 2006/0264819 A1* | 11/2006 | Fischer et al. ............. 604/95.04 |
| 2008/0021535 A1 | 1/2008 | Leopold et al. |
| 2009/0204197 A1 | 8/2009 | Dorn et al. |
| 2010/0087906 A1 | 4/2010 | Dorn et al. |
| 2010/0145430 A1 | 6/2010 | Wubbeling et al. |
| 2010/0286756 A1 | 11/2010 | Dorn et al. |

FOREIGN PATENT DOCUMENTS

| | | | |
|---|---|---|---|
| EP | 1095634 | A2 | 5/2001 |
| EP | 1103281 | A2 | 5/2001 |
| EP | 1890644 | A1 | 2/2008 |
| GB | 453944 | A | 9/1936 |
| JP | 07315147 | A | 12/1995 |
| JP | 2002301161 | A | 10/2002 |
| MX | 298767 | | 5/2012 |
| WO | 9639998 | | 12/1996 |
| WO | 0041525 | A2 | 7/2000 |
| WO | 0134061 | A1 | 5/2001 |
| WO | 0156504 | A1 | 8/2001 |
| WO | 0187180 | A2 | 11/2001 |
| WO | 0215820 | A2 | 2/2002 |
| WO | 0245622 | A2 | 6/2002 |
| WO | 02087470 | A1 | 11/2002 |
| WO | 03002019 | A2 | 1/2003 |
| WO | 03002020 | A2 | 1/2003 |
| WO | 03003944 | A2 | 1/2003 |
| WO | 2004062458 | A2 | 7/2004 |
| WO | 2005053574 | A2 | 6/2005 |
| WO | 2005072652 | A1 | 8/2005 |
| WO | 2006113869 | A2 | 10/2006 |
| WO | 2006133959 | A1 | 12/2006 |
| WO | 2006133960 | A1 | 12/2006 |
| WO | 2007004221 | A1 | 1/2007 |
| WO | 2008031103 | A2 | 3/2008 |

OTHER PUBLICATIONS

PCT/EP2006/005805 filed Jun. 16, 2006 International Preliminary Report on Patentability dated Jun. 12, 2007.
PCT/EP2006/005805 filed Jun. 16, 2006 Search Report dated Oct. 20, 2006.
PCT/EP2006/005805 filed Jun. 16, 2006 Written Opinion dated Oct. 20, 2006.
PCT/EP2006/005806 filed Jun. 16, 2006 International Preliminary Report on Patentability dated Dec. 17, 2007.
PCT/EP2006/005806 filed Jun. 16, 2006 Search Report dated Sep. 27, 2006.
PCT/EP2006/005806 filed Jun. 16, 2006 Written Opinion dated Sep. 27, 2006.
PCT/EP2006/005807 filed Jun. 16, 2006 International Preliminary Report on Patentability dated Dec. 17, 2007.
PCT/EP2006/005807 filed Jun. 16, 2006 Search Report dated Sep. 27, 2006.
PCT/EP2006/005807 filed Jun. 16, 2006 Written Opinion dated Sep. 27, 2006.
PCT/EP2009/066313 filed Dec. 3, 2009 International Preliminary Report on Patentability dated Nov. 29, 2010.
PCT/EP2009/066313 filed Mar. 12, 2009 Search Report dated Mar. 25, 2010.
PCT/EP2009/066313 filed Mar. 12, 2009 Written Opinion dated Mar. 25, 2010.
PCT/EP2009/066314 filed Dec. 3, 2009 International Preliminary Report on Patentability dated Mar. 3, 2011.
PCT/EP2009/066314 filed Dec. 3, 2009 Search Report dated Mar. 5, 2010.
EP 06743169.2 filed Jun. 16, 2006 Office Action dated Apr. 20, 2011.
EP 07787316.4 filed Jul. 10, 2007 Office Action dated Dec. 23, 2011.
U.S. Appl. No. 11/917,303, filed Sep. 19, 2008 Notice of Allowance dated Aug. 10, 2012.
U.S. Appl. No. 11/917,431, filed Dec. 8, 2009 Non-Final Office Action dated Mar. 6, 2012.
U.S. Appl. No. 12/630,098, filed Dec. 3, 2009 Non-Final Office Action dated Apr. 4, 2012.
U.S. Appl. No. 11/917,431, filed Dec. 8, 2009 Non-Final Office Action dated Apr. 2, 2013.

* cited by examiner

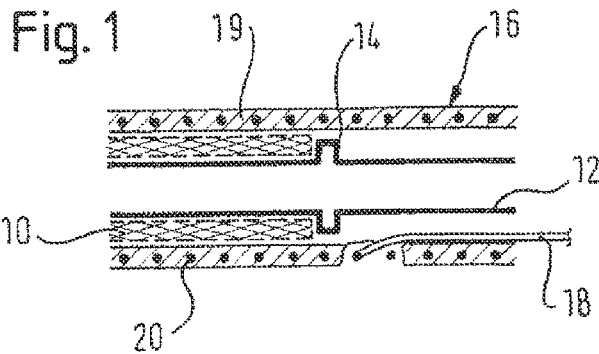
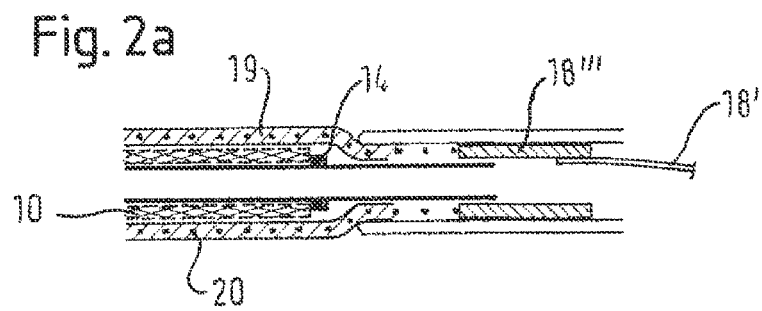
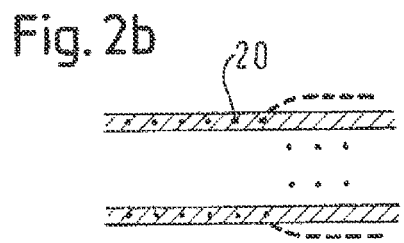
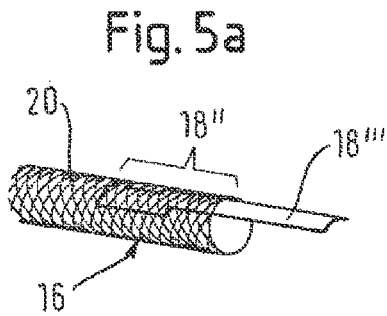
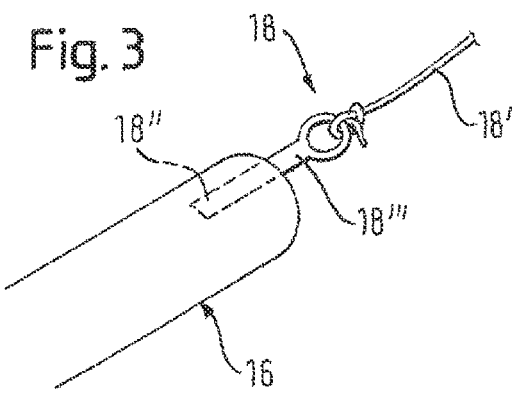
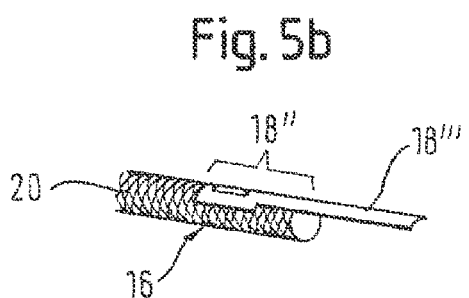

ue to the higher friction forces between the greater contact surface area of the longer implant and the outer sheath, the retracting force needed to retract the outer sheath will necessarily increase with the length. This is particularly noticeable for covered stent grafts, where the friction with the outer sheath is large, as compared with an uncovered stent. Since a greater force has to be applied, the possibility arises that the inner shaft may deflect or move under compression, as ten-
RETRACTABLE CATHETER

PRIORITY

This application claims the benefit of priority to U.S. Provisional Patent Application No. 61/119,668, filed Dec. 3, 2008, and to U.K. Patent Application No. 0822106.1, filed Dec. 3, 2008, each of which is incorporated by reference into this application as if fully set forth herein.

FIELD OF THE INVENTION

This invention relates to a retractable catheter preferably for use as an outer sheath in an implant catheter delivery system, and to a method of manufacturing a retractable catheter. Such a catheter is preferably sized to be inserted in a bodily lumen. Such a retractable catheter includes a pull element connected at its distal end to an elongate tubular sheath.

BACKGROUND ART

Conventional implant catheter delivery systems comprise an inner shaft that extends from a proximal end to a distal end of the system and carries on its distal end a self expanding implant. A longitudinal tubular sheath lies radially outside the implant to retain the implant in the catheter delivery system until the self expanding stent is to be released.

In WO 2006/133959, which is incorporated by reference in its entirety into this application, there is generally shown a catheter device having such a construction. During a medical procedure, the catheter device is pushed distally into a bodily lumen until the implant is disposed at a pre-determined delivery position. To allow the implant to expand at the delivery position, the outer sheath has to be retracted. For this reason the sheath is connected to a pull wire which is pulled by means of a device to apply a pull force to the wire and, thus, to the outer sheath. To connect the wire to the outer sheath, commonly there is used an outer ring and an inner ring, the outer ring radially outside the outer sheath and being crimped or swaged onto the inner ring which is radially inside the outer sheath. The wire can then be connected to the inner ring, while the outer ring is clamped onto the inner ring, fastening both rings and the wire onto the sheath. When the wire is pulled, the sheath is retracted from where it surrounds the implant and the inner shaft, releasing the implant to expand.

Another possibility shown in WO 2006/133959 for fastening the wire relative to the outer sheath is to provide two outer rings outside the sheath, one on each side of an inner ring inside the sheath, to which the pull wire is fastened. The two outer rings are clamped onto the outer sheath, one proximal and one distal to the inner ring, to prevent relative movement between the outer sheath and the inner ring. In this way the outer sheath is connected to the pull wire by clamping it on either side of the inner ring, to move with the inner ring when the pull wire is retracted.

The implants which are to be delivered can be of a variety of lengths, and some may be quite long, for example up to 120 mm in length and 10 mm in diameter. With a longer implant, due to the higher friction forces between the greater contact surface area of the longer implant and the outer sheath, the retracting force needed to retract the outer sheath will necessarily increase with the length. This is particularly noticeable for covered stent grafts, where the friction with the outer sheath is large, as compared with an uncovered stent. Since a greater force has to be applied, the possibility arises that the inner shaft may deflect or move under compression, as tension is applied to the pull wire. The thickness of the inner shaft then must increase to withstand the compressive forces. Larger forces will also tend to break the connection between the pull wire and sheath.

Another disadvantage of such an arrangement is that the diameter of the outer sheath has to be at least large enough, for the inner shaft, the stent and the inner ring to be accommodated in the sheath. Furthermore, the outer rings increase the thickness of the device as well, at least if one is clamped directly on the inner ring, and may distort the outside surface of the outer sheath. Since an application of such an implant catheter delivery system is for delivery of stents by advancing the catheter system into a bodily lumen, a thicker diameter reduces the range of possible treatment opportunities, especially in the narrow confines of a patient's vasculature, or may give rise to a risk of injury as the catheter system is advanced.

SUMMARY OF THE INVENTION

According to a first aspect of the present invention, there is provided A retractable catheter preferably for use in an implant delivery system, the catheter comprising: an elongate tubular sheath made of a relatively flexible material; and a pull element for transmitting a pull force to the sheath to retract it longitudinally, characterized in that: the pull element comprises an end portion disposed in the relatively flexible material, wherein at least the thickness of the end portion is substantially less than its length.

Since the pull element is embedded in the relatively flexible material, even large friction forces between the tubular sheath and the pull element can be overcome, without the need to add further connecting or reinforcing elements, which can provide the catheter with a bigger gap between the inner catheter and the outer sheath for the same overall outside diameter. Additionally, this reduces the number of components in the assembly, so that material and labour costs can be decreased, and the assembling process is facilitated.

Preferably, at least part of the end portion of the pull element is a plate member. More preferably, the end portion is encased within the relatively flexible material between radially inner and outer surfaces of the tubular sheath. In one preferred embodiment, at least part of the end portion is the flattened end of a wire. These arrangements can increase the contact surface area between the flexible material of the sheath and the end portion, improving the bond strength therebetween.

In preferred embodiments, the end portion comprises a stepped and/or tapered portion, in its width and/or thickness directions, along its length. The stepped and/or tapered portion may increase the width and/or the thickness of the end portion in a direction from the proximal end to the distal end of the end portion. The end portion may comprise protrusions, at the distal and/or proximal ends, in the width and/or thickness directions. These step portions or tapered portion again increase the friction and the force transmission between the end portion and the outer sheath. In particular, if these portions increase the width and/or thickness in a direction from the proximal end to the distal end of the end portion, it can be firmly anchored in the relatively flexible sheath material.

Preferably, the end portion is at least at its distal end at least partially tube shaped. This matches the shape of the sheath and again the friction is further increased due to a greater contact surface.

In preferred embodiments, the end portion has a rougher surface than a more proximal portion of the pull element, preferably an Ra surface roughness of between 10 μm and 25 μm. Similarly, or to provide the roughness, the end portion may comprise, at least on a surface which faces radially inwardly or outwardly in the tubular sheath, protrusions and/or micro-protrusions. In the same way, the end portion may comprise, at least on a surface which faces radially inwardly or outwardly in the tubular sheath, recesses and/or micro-recesses. Instead of or additionally thereto, the end portion may be perforated with holes and/or micro-holes. These surface treatments can increase the bond contact area between the pull element and sheath, and so improve force transmission therebetween and increase the bond strength.

Embodiments of the retractable catheter may further comprise a reinforcing structure which is embedded in the flexible material of the elongate tubular sheath. The end portion may be connected to the reinforcing structure, preferably by welding. Preferably, the end portion is disposed at least partially radially inside and/or outside the reinforcing structure in the tubular sheath.

In preferred embodiments, the end portion can comprise steel, plastic, carbon fibre compound and/or glass fibre compound.

In further preferred embodiments, the end portion can exhibit a changing thickness or a substantially continuous thickness.

According to a second aspect of the present invention, there is provided a method of manufacturing a retractable catheter comprising the steps of: —providing a pull element having an end portion, the end portion having a thickness less than its length and width dimensions; and —forming an elongate tubular sheath of relatively flexible material with the end portion disposed therein.

Preferred embodiments of the method comprise the further steps of: —providing an inner layer of relatively flexible material; —positioning the end portion on the outside of the inner layer; and —applying an outer layer of relatively flexible material on the inner layer and the end portion to encase the end portion between the inner and outer layers.

Further preferred embodiments of the method comprise the further steps of: —providing a reinforcing structure; and —disposing the end portion at least partially radially inside and/or outside the reinforcing structure, whereby said reinforcing structure is disposed in the relatively flexible material when said elongate tubular sheath is formed.

BRIEF DESCRIPTION OF THE DRAWINGS

To enable a better understanding of the present invention, and to show how the same may be carried into effect, reference will now be made, by way of example only, to the accompanying drawings, in which:—

FIG. 1 shows a distal end of an embodiment of a retractable catheter according to the present invention;

FIGS. 2a and 2b show a distal end of another embodiment of a catheter according to the present invention and possible arrangement to connect the reinforcing structure with the pull element;

FIG. 3 is a perspective view of a distal end of an embodiment of a catheter according to the present invention;

FIGS. 5a and 5b show an embodiment in which the end portion of a pull element is embedded into the wall of an outer sheath which is provided with a braided reinforcing layer.

DETAILED DESCRIPTION

Figure 4A:
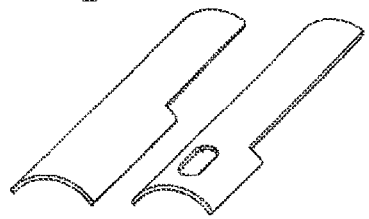
FIGS. 4a to 4h are different examples of an end portion which can be used in embodiments of the present invention.

In the following, the expressions "distal", meaning away from the operator's side, and "proximal", meaning towards the operator's side, are used, and define also respective directions which are substantially along the longitudinal axis of the delivery catheter.

Referring to FIG. 1, a self-expanding implant 10, known as a stent, is placed around a shaft tube 12 and abuts on an abutment member 14 that can be formed integrally with the shaft tube 12 or can be a separate member, as for example a ring clamped or otherwise fixed on the shaft tube. The shaft tube 12 can be strengthened by a supporting member, such as a steel spring wound tightly to resist compression but to allow off-axis flexibility, in particular if the implant is very long.

Around this arrangement is disposed an outer catheter sheath 16 that covers the distal end portion of the shaft tube 12 and the implant 10. The outer catheter sheath 16 extends longitudinally from a distal end in a proximal direction. The outer sheath 16 may extend substantially the whole length of the delivery system, but preferably is not significantly longer than is needed merely to cover the implant 10. A pull element 18, such as a wire, a strand, a tube or another element, capable of transmitting a pull force and flexible enough to follow the catheter path, is connected to the outer sheath 16 at or near its proximal end. The pull element 18 can consist of a single part, or may contain two or more elements, which then are fixed together. The pull element may include a wire, which usually leads to a hand device (not shown) which is responsible for generating the pull force to retract the outer catheter sheath 16 relative to the shaft tube 12.

As shown schematically in FIG. 1, pull wire 18 can be connected to a reinforcing structure 20 embedded in the outer catheter sheath, at an exposed portion where the outer catheter sheath bulk material is not formed or is removed to expose the reinforcing structure 20. There are, however, many different possibilities to connect the pull element 18 to the outer sheath 16. Some other exemplary configurations are discussed in the following.

The outer sheath comprises, at least at its distal end, a flexible material 19 such as polyamide, PEBAX and/or PTFE. The flexible material should have characteristics enabling the sheath to be bendable enough for moving through sharp curvatures in a bodily lumen like the vascular system of a patient.

In this flexible material 19 can be embedded a reinforcing structure 20 to provide the outer sheath 16 with a better strength. In particular, the reinforcing structure 20 should be strong under tension in the longitudinal direction of the outer sheath 16, and will thus resist necking, whereby its diameter reduces, when pulled longitudinally. The reinforcing structure 20 is made of a relatively inextensible material compared to the flexible material 19, and may be, for example, stainless steel or carbon fibre or glass fibre compounds. The reinforcing structure 20 is, thus, ideally suited to transmit the load applied by pulling the pull element 18 to the outer sheath 16, along the length thereof. Of course the reinforcing structure 20 has a construction that enables it still to be bent for movement around the above-mentioned sharp curvatures. Preferred reinforcing structures are wound coils, braidings, other net-shaped or cage structures, or just arrangements of connected wires. However, in other examples, the flexible material 19 can be resistant enough lengthwise stretching to work without a reinforcing structure 20 and a reinforcing structure is not necessarily needed.

In embodiments of the first aspect of the invention, the pull element 18 is connected directly to the reinforcing structure 20, which enables the outer sheath 16 to withstand a greater load applied to the sheath 16 through the pull element 18, without risk of breaking the connection between the pull element 18, and the flexible material 19 of the sheath, and facilitating a low-profile interconnection that does not significantly increase the sheath diameter.

A reliable connection method is to connect the pull element onto the braiding thermally. This allows a very well defined connection to be made and reduces the contact area that is needed to create a resilient connection. Therefore, a thermal connection method, like laser, resistance or gap welding, provides a secure connection and can transmit high pull forces. To improve the thermal connection, a support element, such as a weld ring, can be applied to the connection area. For example, a pull element 18 can be welded onto the reinforcing structure 20 by using the weld ring. Using such a supporting element can improve the force distribution around the sheath circumference, since the weld ring can be welded at almost equal distances around its circumference, and can provide force transmission to the reinforcing structure 20 through more than one transmission point. If the spacing of the welding points is generally equal, the force transmission into the reinforcing structure 20 and, thus, in the outer sheath 16 will be generally equal as well, and this can provide a very consistent force transmission and smooth retraction movement of the outer sheath 16.

To connect the pull element 18 to the reinforcing structure 20, with or without thermal connection, the pull element 18 can be at least partially woven into the reinforcing structure 20. For example, a wire pull element can be threaded through a braiding reinforcing structure. Alternatively, instead of or in addition to a thermal or mechanical fixation, the pull element 18 can be adhered directly to the reinforcing structure 20, for example by using adhesive means.

Furthermore, as illustrated in FIG. 2a, the pull element 18 may include a connection link 18''' at its distal end, which can be connected to the reinforcing structure 20. A support element can be used in conjunction with the connection link 18''', but the connection link can also provide the function of the support element. Such a connection link could consist of a tube 18''' which is connected at its distal end to the outer sheath 16 and at its proximal end to a wire 18' that leads out of the catheter. Of course, the shape of the connection link 18'' is not limited to a tubular shape. Another possible shape of the connection link 18''' is shown in FIG. 3, with a connection to pull wire 18' proximal of the flexible material of outer sheath 16.

It is preferable to connect the pull element 18 to an exposed portion of the reinforcing structure, so that the pull element 18, the connection link 18'' and/or the support element (not shown) can be connected directly thereto. Usually, a reinforced outer sheath 16 is formed with the reinforcing structure 20 completely embedded in the flexible material 19 of the outer sheath 16. Therefore, with a pre-formed reinforced sheath, it is necessary to remove a part of the flexible material 19 to gain access to the reinforcing structure 20 and to make it possible to connect the pull element directly to the reinforcing structure. The removal of the flexible material 19 can be done in different ways, such as by cutting and/or by thermal means, for example welding. A preferred method, however, is to burn a portion of the flexible material 19 off the reinforcing structure 20 using a laser.

Alternatively, an outer sheath 16 might be formed with an exposed part of the reinforcing structure 20 arranged at a proximal end of the outer sheath 16. In one example, the reinforcing structure 20 is only partially embedded in the flexible material 19, and has a portion with a smaller or larger diameter than the diameter of the sheath, outside the flexible material of the tubular sheath wall (see FIG. 2b, dotted and dashed lines respectively).

With a portion of the reinforcing structure exposed, it may be desirable to provide an outer layer, to cover the exposed portion, after the pull element 18 has been connected thereto, to render the sheath atraumatic. As further examples, the exposed portion of the reinforcing structure 20 which the pull element is connected to can be covered by applying an extrusion mass onto this portion, by sticking an adhesive tape onto the exposed portion and/or by providing the exposed portion with a cover tube or similar element. Such shape tape or cover tube could, for example, be made of a shape memory alloy.

The connection link 18'' as well as the support element can be made from different materials known to the skilled person, such as stainless steel, phynox, titanium, shape memory alloy, such as Nitinol, and/or any other material which is biocompatible and has the requisite mechanical properties.

In embodiments of the second aspect of the invention, no reinforcing structure 20 is necessarily incorporated in the flexible material 19 of the outer sheath, although by preference such a reinforcing structure may be provided to these embodiments as well, since the reinforcing structure 20 improves the strength of the outer sheath 16.

In these embodiments, the pull element 18 comprises a distal end portion 18'' which has a thickness less than its width and length dimensions and is embedded in the outer catheter sheath 16. The end portion preferably is or includes all or part of a plate member 18'', and is disposed in the relatively flexible material 19 of the elongate tubular sheath 16. The end portion may be of many different shapes, as can be seen in the examples of FIGS. 4a-4h. These shapes can comprise straight, rectangular or stepped sides, as well as tapered sides. A combination of straight and tapered sides is possible as well. Preferably, any end portion can be provided with protruding portions at its distal and/or proximal ends. The protruding portions may protrude left and right (corresponding to the circumferential directions of the tubular sheath wall when embedded therein) as can be seen, for example, in FIGS. 4e and 4f. The protrusions may also or instead protrude in an upward or downward direction with respect to the lengthwise direction of the end portion 18'' (corresponding to a radially outward or inward direction of the tubular sheath wall when embedded therein). Another possible shape is a tubular end portion with a closed circumference or a part tubular end portion with an incomplete circumference. All such plate shapes may exhibit a curvature to match the tubular form of the elongate outer sheath 16.

With specific reference to FIG. 4a, there is shown a pair of plate members which can be used to form the end portion of the pull element 18. As seen in FIG. 4a, the distal end of the plate member is that at the front-left of the perspective view, whilst the proximal end is shown at the far-right of the perspective view. (The same orientation is shown in FIGS. 4a to 4d, but is reversed in FIGS. 4e to 4h, although in fact the plate members may be embedded into the elongate outer sheath 16 either way round, according to the particular application.) The plate member on the left hand side of FIG. 4a is formed with a stepped region approximately half way along its length, at which the width of the plate member decreases from being relatively wide at the near, distal end to being relatively thin at the far, proximal end. As can be seen, the plate member is curved about an axis in the longitudinal direction, to match the curvature of the tube wall of the elongate outer sheath 16. The plate member shown on the right hand side of FIG. 4a is similarly formed with a stepped width, reducing from a greater width near the distal end to a reduced width in the center and proximal portions. This right hand side plate member is similarly formed with a curvature to match the tubular wall of the elongate outer sheath 16, and is additionally provided with a through-hole in the plate member near to the distal end, through which the relatively flexible material of the sheath outer wall can be bonded between the radially internal and radially external sides of the plate member 18", when embedded in the outer sheath 16.

Figure 4B:
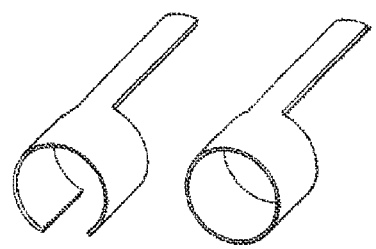

Two further plate members are illustrated in FIG. 4b, the right hand member having a tubular (complete tubular) distal portion connected to a proximally extending plate having a relatively minor circumferential extent. The plate member on the left hand side of FIG. 4b is similarly shaped, except that the distal tubular portion is only part-tubular, not extending fully around the circumference of the tubular shape corresponding to the wall of the elongate outer sheath 16.

Figure 4C:
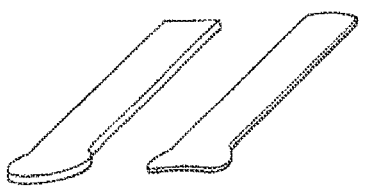
Figure 4D:
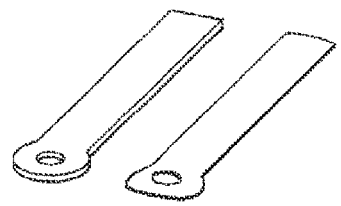

FIGS. 4c to 4h show pairs of plate members having the same overall shape on their major surfaces, in which the left hand plate member in each illustrated pair is a flat plate member, and in which the right hand plate member in each pair has been formed so as to be curved about its longitudinal axis to match the curvature of the tubular wall of the elongate outer sheath 16. The plate members in FIG. 4c are substantially rectangular in shape, having a bulbous rounded distal end attached thereto, projecting partially in the width wise (circumferential) directions. The plate members illustrated in FIG. 4d are of substantially the same shape as those in FIG. 4c, although with a through-hole formed in the substantially circular distal end portion of the plate member between the upper and lower surfaces corresponding to the radially outer and inner surfaces of the member when it is embedded into the elongate outer sheath 16.

Figure 4E:
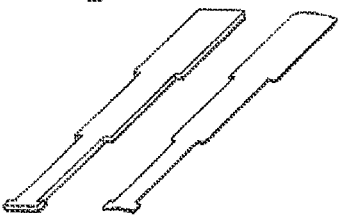
Figure 4F:
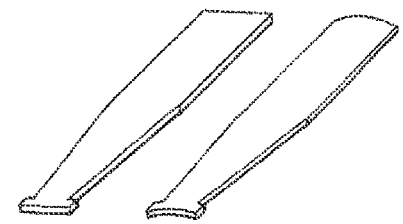
Figure 4G:
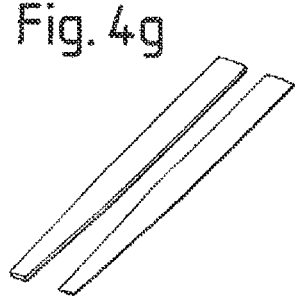
Figure 4H:
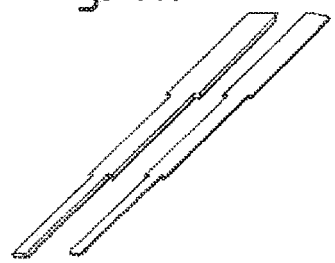

In FIG. 4e, the plate members are stepped to have a width dimension that increases between a proximal region and a central region, and again between the central region and a distal region of the plate member. Left and right (circumferentially extending) projections are provided at the proximal end of the plate members to facilitate connection to the proximal portion of the pull element 18, such as a pull wire 18'. The plate members of FIG. 4f are similarly provided with projections at the proximal end, and are tapered from a narrow circumferential width at the proximal end to a wider circumferential width near the central portion, which continues to the distal end of the plate member. The plate members shown in FIG. 4g have a similar form to those shown in FIG. 4f, whilst the plate members shown in FIG. 4h have a similar form to the plate members shown in FIG. 4e, except that in FIGS. 4g and 4h the proximal left and right projections are omitted.

On the one hand, the end portions, and in particular those having shapes with a changing width (stepped or tapering shapes), can form part of the unitary pull element 18 that extends to the proximal end of the catheter, in which case no pull wire is required as part of the pull element. In particular, the shapes of FIGS. 4e-4h can be adapted to extend to the proximal end of the catheter and to act as the complete pull element 18. On the other hand, the end portions may be connected to a pull wire 18' as an independent member, to form pull element 18. In this case there may be provided an intermediate connecting portion that facilitates the connection of the pull wire 18' to the end portion 18".

Another possibility for forming the pull element is to provide a wire with a flattened end, and to incorporate the flattened end at least partially in the flexible material of the outer sheath 16 as the end portion 18". The flattened end of the wire, in whole or in part, acts as the end portion, whereas the wire itself is acting as a pull wire 18'.

The end portion 18" may comprise one or more holes or recesses to increase the bond strength between the flexible material 19 and the end portion 18" embedded therein. This enables the pull element 18 to transmit sufficient force to the sheath 16, even by merely being embedded in the relatively flexible material 19, to enable the sheath 16 to be retracted by pulling on the pull element 18. Another option could be to provide protrusions on the major surfaces (radially inwardly or outwardly facing surfaces) of the end portion, with a similar effect. The holes, the recesses and/or the protrusions can be micro-dimensional. Such micro dimensional holes, recesses and/or protrusions may give the surface a certain surface roughness, or the surface may be otherwise roughened, preferably to have an Ra surface roughness of between 10 μm and 25 μm on the major surfaces of the end portion 18'. By treating the surface structure of the embedded end portion the bond strength between the end portion 18" and the flexible material 19 can be improved, to allow the pull element 18 to impart a higher tensile force to the sheath 16, as described above. For this reason the surfaces of the end portion 18" can be corrugated, sand plastered and/or edged or otherwise chemically treated or coated, as appropriate.

The shape of the embedded end portion could be of continuous width and continuous thickness, of tapered or stepped width and a continuous thickness, of a continuous width and tapered or stepped thickness, or of tapered and/or stepped width and thickness. The end portion may be so formed by a mechanical press, by rolling, by laser cutting or by grinding, for example.

The material of the pull element and/or of the end portion may comprise stainless steel, plastic, carbon fiber compound and/or glass fiber compound.

If, in the distal end of the catheter sheath 16, there is no reinforcing structure 20 then the end portion 18" can be simply embedded in the relatively flexible material 19 of the elongate outer catheter sheath 16. If there is provided a reinforcing structure 20 incorporated into the outer catheter sheath 16, the end portion can be placed underneath (radially inside when embedded in the tubular sheath wall) the reinforcing structure 20 or above (radially outside where embedded in the tubular sheath wall) the reinforcing structure 20. These two arrangements are shown in FIGS. 5a and 5b, respectively. The incorporation of the end portion 18" into the material 19 of the outer sheath alone, however, is enough to transmit the necessary tensile force to the outer sheath 16 to retract it.

Alternatively, the end portion 18" may be connected to the reinforcing structure in the same manner as in the first aspect of the invention discussed above. For example, the end portions 18" can be laser, resistance or gap welded to the reinforcing structure 20, and/or the end portion 18" could be woven into the reinforcing structure 20. In one embodiment, the flattened end of a wire can be threaded through the strands of a braided reinforcing structure, as mentioned before.

The surface of the non-embedded parts of the pull element, i.e. not the end portion 18", is preferably treated to achieve a low friction between those parts of the pull element 18 (particularly any pull wire 18') which lead to the stent deployment actuator (not shown) and the surrounding components of the stent delivery system. Thus, the pull element 18 can be treated with PTFE, such as to form a PTFE coated pull wire.

Preferred methods for manufacturing and assembling the retractable sheaths of the present invention will now be described.

In one preferred method, an outer sheath is provided comprising a reinforcing structure 20 formed in the tubular wall of the outer sheath. A proximal portion of the relatively flexible material forming the wall of the outer sheath 16 is removed to expose a portion of the reinforcing structure 20. The relatively flexible material of the outer sheath 16 is preferably removed by burning it off from the reinforcing structure 20 using a laser. Alternatively, the relatively flexible material may be removed by mechanical or chemical means, or through alternative burning or melting methods. Pull element 18 is then attached to the exposed portion of the reinforcing structure 20, to form a connection directly with the reinforcing structure 20 by which the outer sheath 16 may be retracted by applying a tensile pull force to the pull element 18. In preferred embodiments, where the reinforcing structure 20 and the pull element 18 are both formed from biocompatible metal, the pull element 18 can be laser or spot welded to the reinforcing structure 20.

The pull element 18 may simply be provided in the form of a pull wire 18' to be welded directly to a portion of the reinforcing structure 20. Alternatively, where a connection link 18''' is provided as part of the pull element 18, the pull wire 18' can be connected to the connection link 18''', which is joined to the reinforcing structure 20. Whether a pull wire 18' is connected directly to the reinforcing structure 20 or a connection link 18''' is used, a weld ring may also preferably be used in order to facilitate welding of the pull element 18 to the reinforcing structure 20. This is particularly preferable where the reinforcing structure 20 is metal braiding, as the ends of the different strands of the braiding around the circumference of the reinforcing structure can all be connected to the weld ring so that tensile retraction forces transmitted through the pull element 18 will be distributed and applied relatively evenly around the circumference of the reinforcing structure, and consequently along and through the outer sheath 16.

After the pull element 18 has been connected to the reinforcing structure 20, it may be desirable to cover over the connection region, for example by extruding an outer layer of relatively flexible material to cover the exposed portion of the reinforcing structure 20 and the connection region where the pull element 18 and reinforcing structure 20 are joined. Alternative means may otherwise be provided for rendering the connection atraumatic, for example by providing a supplementary outer sheath layer, such as a shrink tube, to be shrunk down over the outer sheath 16 and pull element 18.

In another preferred method for forming the retractable catheter, a reinforced outer sheath 16 is provided by first forming an inner layer of relatively flexible material about a mandrel, for example by extrusion. Reinforcing structure 20 is then applied onto the inner layer of relatively flexible material along all or a portion of the length of the inner layer. An outer layer of relatively flexible material is then provided to cover the reinforcing structure 20 and the inner layer of relatively flexible material, so as to encapsulate the reinforcing structure 20 between the inner and outer layers which together make up the outer sheath 16. The inner and outer layers of the outer sheath 16 preferably fused together between gaps or interstices in the reinforcing structure 20. The fusion between inner and outer layers may be achieved during the extrusion of the outer layer onto the inner layer and reinforcing structure 20, or maybe achieved through subsequent heat treatment of the laminated structure. Alternatively, the reinforced sheath produced in this manner may be manufactured in a substantially continuous process by co-extruding the inner and outer layers onto the mandrel at the same time as the reinforcing structure 20 is supplied in-between the two layers. In either case, the mandrel is then removed, for example by allowing it to deflate or contract radially inwardly, to leave the enforced sheath structure. This sheath structure can be treated according to the method above, by removing part of the inner or outer layers to expose a portion of the reinforcing structure 20 to connect it to a pull element 18. Alternatively, the reinforcing structure 20 may be provided so as to extend beyond the inner and/or outer layers of the relatively flexible material of the outer sheath 16, thereby forming the sheath with an exposed portion of reinforcing structure 20, to which the pull element 18 can be connected. As a further alternative, the pull element 18 can be first connected to the reinforcing structure 20, prior to the reinforcing structure being incorporated between the inner and outer layers of the relatively flexible material. According to this method, the connection between the pull element 18 and the reinforcing structure 20 will become encapsulated between the inner and outer layers of relatively flexible material of the outer sheath 16 during the aforementioned layering of these structures onto a mandrel.

In a further preferred method, the pull element 18 comprises a plate member. Whether any reinforcing structure 20 is provided or not, the plate member is encapsulated within the relatively flexible material of the outer sheath 16, by first layering an inner layer of material onto a mandrel, placing a portion of the plate member onto the inner layer, and then subsequently providing an outer layer of relatively flexible material to cover the inner layer and the plate member, so as to encapsulate end portion 18'' of the pull element 18 in the flexible material of the outer sheath 16. As noted above, the inner and outer layers of flexible material are preferably extruded onto the mandrel and become fused together to form the outer sheath 16.

In general, the same relatively flexible material may be used for the inner and outer layers of the outer sheath 16, or two different relatively flexible materials may be used for the respective layers.

What is claimed is:

1. A retractable catheter, comprising:
   an elongate tubular sheath made of a relatively flexible material; and
   a pull element for transmitting a pull force to the sheath to retract it longitudinally, the pull element including an end portion disposed in the relatively flexible material, wherein at least the thickness of the end portion is substantially less than its length, wherein at least part of the end portion is a plate member having a stepped portion, in its width and/or thickness directions, along its length, the stepped portion increasing from a proximal end to a distal end thereof, and wherein the end portion distal end is at least partially tube-shaped.

2. The retractable catheter according to claim 1, wherein the end portion is encased within the relatively flexible material between radially inner and outer surfaces of the tubular sheath.

3. The retractable catheter according to claim 1, wherein at least part of the end portion is the flattened end of a wire.

4. The retractable catheter according to claim 1, wherein the end portion comprises protrusions, at the distal and/or proximal ends, in the width and/or thickness directions.

5. The retractable catheter according to claim 1, wherein the end portion has a rougher surface than a more proximal portion of the pull element, the Ra surface roughness of the end portion being in the range from about 10 μm to about 25 μm.

6. The retractable catheter according to claim 1, wherein the end portion comprises, at least on a surface which faces radially inwardly or outwardly in the tubular sheath, protrusions and/or micro-protrusions.

7. The retractable catheter according to claim 1, wherein the end portion comprises, at least on a surface which faces radially inwardly or outwardly in the tubular sheath, recesses and/or micro-recesses.

8. The retractable catheter according to claim 1, wherein the end portion is perforated with holes and/or micro-holes.

9. The retractable catheter according claim 1, further comprising a reinforcing structure which is embedded in the flexible material of the elongate tubular sheath.

10. The retractable catheter according to claim 9, wherein the end portion is connected to the reinforcing structure.

11. The retractable catheter according to claim 10, wherein the end portion is disposed radially outside the reinforcing structure in the tubular sheath.

12. The retractable catheter according to claim 1, wherein the end portion material is selected from the group consisting of steel, plastic, carbon fibre compound, glass fibre compound, and combinations thereof.

13. The retractable catheter according to claim 1, wherein the end portion has a substantially continuous thickness.

14. An implant delivery system, comprising:
  - an elongate tubular outer sheath made of a relatively flexible material and including a reinforcing structure embedded in the flexible material, the outer sheath covering an expandable implant; and
  - a pull element for transmitting a pull force to the outer sheath to retract it longitudinally to uncover the expandable implant, the pull element including an end portion disposed in the relatively flexible material, wherein at least the thickness of the end portion is substantially less than its length, wherein at least part of the end portion is tapered and/or stepped in its width and/or thickness directions along its length, with the width and/or thickness increasing from a proximal end to a distal end thereof.

15. The implant delivery system according to claim 14, wherein the outer sheath is not significantly longer than necessary to cover the expandable implant.

16. The implant delivery system according to claim 14, wherein the end portion is encased within the relatively flexible material between radially inner and outer surfaces of the outer sheath.

17. The implant delivery system according to claim 14, wherein the end portion is connected to the reinforcing structure.

18. The implant delivery system according to claim 14, wherein the end portion distal end is at least partially tube-shaped.

19. A retractable catheter, comprising:
  - an elongate tubular sheath made of a relatively flexible material; and
  - a pull element for transmitting a pull force to the sheath to retract it longitudinally, the pull element including an end portion disposed in the relatively flexible material, wherein at least the thickness of the end portion is substantially less than its length, wherein at least part of the end portion is a plate member having a stepped portion, in its width and/or thickness directions, along its length, the stepped portion increasing from a proximal end to a distal end thereof, and wherein the end portion comprises protrusions, at the distal and/or proximal ends, in the width and/or thickness directions.

20. A retractable catheter, comprising:
  - an elongate tubular sheath made of a relatively flexible material; and
  - a pull element for transmitting a pull force to the sheath to retract it longitudinally, the pull element including an end portion disposed in the relatively flexible material, wherein at least the thickness of the end portion is substantially less than its length, wherein at least part of the end portion is a plate member having a stepped portion, in its width and/or thickness directions, along its length, the stepped portion increasing from a proximal end to a distal end thereof, and wherein the end portion has a rougher surface than a more proximal portion of the pull element, the Ra surface roughness of the end portion being in the range from about 10 µm to about 25 µm.

21. A retractable catheter, comprising:
  - an elongate tubular sheath made of a relatively flexible material; and
  - a pull element for transmitting a pull force to the sheath to retract it longitudinally, the pull element including an end portion disposed in the relatively flexible material, wherein at least the thickness of the end portion is substantially less than its length, wherein at least part of the end portion is a plate member having a stepped portion, in its width and/or thickness directions, along its length, the stepped portion increasing from a proximal end to a distal end thereof, and wherein the end portion comprises, at least on a surface which faces radially inwardly or outwardly in the tubular sheath, protrusions and/or micro-protrusions.

* * * * *